United States Patent
Liu et al.

(10) Patent No.: US 11,617,556 B2
(45) Date of Patent: Apr. 4, 2023

(54) FAST 3D RADIOGRAPHY WITH MULTIPLE PULSED X-RAY SOURCE TUBES IN MOTION

(71) Applicants: Jianqiang Liu, Campbell, CA (US); Manat Maolinbay, Gilroy, CA (US); Chwen-Yuan Ku, San Jose, CA (US); Linbo Yang, Pleasanton, CA (US)

(72) Inventors: Jianqiang Liu, Campbell, CA (US); Manat Maolinbay, Gilroy, CA (US); Chwen-Yuan Ku, San Jose, CA (US); Linbo Yang, Pleasanton, CA (US)

(73) Assignee: AIX Scan, Inc., Sunnyvale, CA (US)

( * ) Notice: Subject to any disclaimer, the term of this patent is extended or adjusted under 35 U.S.C. 154(b) by 85 days.

(21) Appl. No.: 17/488,539

(22) Filed: Sep. 29, 2021

(65) Prior Publication Data
US 2022/0313188 A1    Oct. 6, 2022

Related U.S. Application Data

(60) Provisional application No. 63/226,508, filed on Jul. 28, 2021, provisional application No. 63/225,194, (Continued)

(51) Int. Cl.
*A61B 6/00*    (2006.01)
*A61B 6/02*    (2006.01)
(Continued)

(52) U.S. Cl.
CPC .............. *A61B 6/541* (2013.01); *A61B 6/025* (2013.01); *A61B 6/032* (2013.01); *A61B 6/035* (2013.01); *A61B 6/0407* (2013.01); *A61B 6/06* (2013.01); *A61B 6/08* (2013.01); *A61B 6/405* (2013.01); *A61B 6/4007* (2013.01);
(Continued)

(58) Field of Classification Search
CPC ........ A61B 6/4007; A61B 6/032; A61B 6/025
See application file for complete search history.

(56) References Cited

U.S. PATENT DOCUMENTS

| | | | |
|---|---|---|---|
| 2009/0080598 A1* | 3/2009 | Tashman | A61B 5/1038 378/11 |
| 2010/0172561 A1* | 7/2010 | Ota | G01N 23/046 378/19 |

(Continued)

*Primary Examiner* — Dani Fox
(74) *Attorney, Agent, or Firm* — Patent PC; Bao Tran

(57) ABSTRACT

An X-ray imaging system with multiple pulsed X-ray source tubes in motion to perform highly efficient and ultrafast 3D radiography is presented. There are multiple X-ray tubes from pulsed sources mounted on a structure in motion to form an array of X-ray tubes. The tubes move simultaneously relative to an object on a pre-defined arc track at a constant speed as a group. Each individual X-ray tube in each individual source can also move rapidly around its static position in a small distance. When a tube has a speed that is equal to group speed but with opposite moving direction, the tube and X-ray flat panel detector are activated through an external exposure control unit so that the tube stay momentarily standstill. It results in much reduced travel distance for each X-ray source tube and much lighter load for motion system. 3D X-ray scan can cover much wider sweeping angle in much shorter time and image analysis can also be done in real time.

20 Claims, 4 Drawing Sheets

Related U.S. Application Data filed on Jul. 23, 2021, provisional application No. 63/224,521, filed on Jul. 22, 2021, provisional application No. 63/222,847, filed on Jul. 16, 2021, provisional application No. 63/220,924, filed on Jul. 12, 2021, provisional application No. 63/214,913, filed on Jun. 25, 2021, provisional application No. 63/209,498, filed on Jun. 11, 2021, provisional application No. 63/194,071, filed on May 27, 2021, provisional application No. 63/188,919, filed on May 14, 2021, provisional application No. 63/182,426, filed on Apr. 30, 2021, provisional application No. 63/175,952, filed on Apr. 16, 2021, provisional application No. 63/170,288, filed on Apr. 2, 2021.

(51) Int. Cl.

| | | |
|---|---|---|
| *G06T 17/00* | (2006.01) | |
| *G01N 23/044* | (2018.01) | |
| *A61B 6/03* | (2006.01) | |
| *A61B 6/06* | (2006.01) | |
| *G01N 23/083* | (2018.01) | |
| *G01N 23/18* | (2018.01) | |
| *G06T 7/00* | (2017.01) | |
| *G06T 11/00* | (2006.01) | |
| *A61B 6/04* | (2006.01) | |
| *G06T 7/11* | (2017.01) | |
| *G16H 10/60* | (2018.01) | |
| *G16H 30/20* | (2018.01) | |
| *G16H 50/20* | (2018.01) | |
| *G06V 10/25* | (2022.01) | |
| *G06V 10/62* | (2022.01) | |
| *A61B 6/08* | (2006.01) | |

(52) U.S. Cl.
CPC .......... *A61B 6/4014* (2013.01); *A61B 6/4021* (2013.01); *A61B 6/4208* (2013.01); *A61B 6/4283* (2013.01); *A61B 6/4405* (2013.01); *A61B 6/4441* (2013.01); *A61B 6/4452* (2013.01); *A61B 6/4476* (2013.01); *A61B 6/4482* (2013.01); *A61B 6/467* (2013.01); *A61B 6/482* (2013.01); *A61B 6/54* (2013.01); *A61B 6/542* (2013.01); *A61B 6/56* (2013.01); *A61B 6/583* (2013.01); *G01N 23/044* (2018.02); *G01N 23/083* (2013.01); *G01N 23/18* (2013.01); *G06T 7/0012* (2013.01); *G06T 7/0016* (2013.01); *G06T 7/11* (2017.01); *G06T 11/003* (2013.01); *G06T 11/006* (2013.01); *G06T 17/00* (2013.01); *G06V 10/25* (2022.01); *G06V 10/62* (2022.01); *G16H 10/60* (2018.01); *G16H 30/20* (2018.01); *G16H 50/20* (2018.01); *A61B 6/4275* (2013.01); *A61B 6/502* (2013.01); *G01N 2223/401* (2013.01); *G06T 2200/24* (2013.01); *G06T 2207/10076* (2013.01); *G06T 2207/10081* (2013.01); *G06T 2207/20081* (2013.01); *G06T 2207/20084* (2013.01); *G06T 2207/30064* (2013.01); *G06T 2207/30096* (2013.01); *G06T 2207/30168* (2013.01); *G06T 2210/41* (2013.01); *G06V 2201/032* (2022.01)

(56) References Cited

U.S. PATENT DOCUMENTS

| | | | |
|---|---|---|---|
| 2012/0076260 A1* | 3/2012 | Kitagawa | G16H 30/40 382/128 |
| 2020/0345318 A1* | 11/2020 | Turner | A61B 6/587 |

\* cited by examiner

FAST 3D RADIOGRAPHY WITH MULTIPLE PULSED X-RAY SOURCE TUBES IN MOTION

The present invention claims priority to Provisional Application Ser. Nos. 63182426 filed on Apr. 30, 2021; 63/226,508 filed Jul. 28, 2021; 63/170,288 filed Apr. 2, 2021, 63/175,952 filed Apr. 16, 2021, 63/194,071 filed May 27, 2021; 63/188,919 filed May 14, 2021; 63/225,194 filed Jul. 23, 2021; 63/209,498 filed Jun. 11, 2021; 63/214,913 filed Jun. 25, 2021; 63/220,924 filed Jul. 12, 2021; 63/222, 847 filed Jul. 16, 2021; 63/224,521 filed Jul. 22, 2021; and U.S. application Ser. No. 17/149,133 filed Jan. 24, 2021, which in turn claims priority to Provisional Ser. 62/967,325 filed Jan. 29, 2020, the content of which is incorporated by reference.

FIELD OF THE INVENTION

This patent specification is in the field of 3D X-ray radiography systems and methods and particularly to using multiple pulsed X-ray sources and X-ray digital flat panel detectors.

BACKGROUND

Digital tomosynthesis (DTS), is a method for performing high-resolution limited-angle tomography at radiation dose levels comparable with conventional radiography. These digital tomosynthesis systems typically use an X-ray source mounted at rotatable arm assembly and a digital flat panel detector next to the rotation center. When tomosynthesis is performed, the X-ray source would need to move in an arc around an object. While the X-ray source moves around the object, a series of low-dose X-ray images are acquired at different angles. The collected data set permits the reconstruction of parallel planes. Each plane is in focus, and those that are out-of-plane tissue images are blurred. Usually, a wider sweep angle would generate more data projections and result in better 3D resolution, but it takes longer. Data processing is manufacturer-specific because different reconstruction algorithms might be used. It should be emphasized that these kinds of digital tomosynthesis systems and methods can also be applied to other X-ray 3D radiography applications such as X-ray 3D chest diagnosis system for COVID, X-ray 3D Non-Destructive Test (NDT) system, and X-ray 3D security inspection system in addition to digital mammography. There are prior arts that are with the single X-ray source and single flat panel to perform X-ray 3D radiography. However, there are disadvantages among prior arts. The main disadvantage is that a single X-ray source takes a very long time to acquire good data projections. It is true for both continuous mode and step-and-shoot mode. In continuous mode, the X-ray source emits X-ray while it is moving; in step-and shoot mode, the X-ray source moves to a location, stops and emits X-ray, and continues moving to the next location. Although all patients hope X-ray imaging could be done as fast as possible, there is a minimum X-ray source travel sweep angle requirement. If the sweep angle is too small so that the X-ray source can travel less and the total time needed is less, then the system will have smaller numbers of data projections. The smaller number of data projections would result in lower depth resolution and loss of details perception. Suppose the sweep angle needs to be large enough for good data projections for better 3D resolution. In that case, a single X-ray source may mechanically travel too long that patients will feel uncomfortable and cannot hold breast standstill anymore. In some cases, a 50-degree sweep would take as long as about half a minute. The second disadvantage is that it is difficult to do real-time reconstruction because the whole thing is slow. Usually, prior art takes tens of seconds to finish sweeping.

SUMMARY

In a first aspect, a system to provide fast 3D radiography using multiple pulsed X-ray source tubes in motion with a primary motor stage moving freely on an arc rail with a predetermined shape; a primary motor that engages with said primary motor stage and controls a speed of the primary motor stage; a plurality of secondary motor stages coupled to said primary motor stage and move along a direction of the arc rail; a plurality of secondary motors, each engaging a secondary motor stage and controlling a speed of secondary motor stage; a plurality of X-ray tubes from X-ray sources each moved by a secondary motor stage; a supporting frame structure that provides housing for the primary motor stage and secondary motor stages; and an X-ray flat panel detector to receive X-ray and send imaging data.

In a second aspect, a method of fast 3D radiography using multiple pulsed X-ray source tubes in motion includes positioning a primary motor stage and one or more secondary motor stages to a predetermined initial location; sweeping the primary motor stage at a predetermined constant speed by said primary motor; oscillating each of the secondary motor stages by a corresponding secondary motor with a predetermined sequence; electrically activating an X-ray source tube and the X-ray flat panel detector when a secondary motor stage moves in an opposite direction to that of the primary motor stage and at a selected speed of the primary motor stage; and acquiring image data from the X-ray flat panel detector.

In another aspect, an X-ray imaging system using multiple pulsed X-ray source tubes in motion to perform ultrafast, high efficiency 3D radiography is presented. In the system, there are multiple pulsed X-ray source tube mounted on a structure in motion to form an array of the source. The multiple X-ray source tubes move simultaneously around an object on a pre-defined track at a constant speed of a group. Each individual X-ray source tube can also move rapidly around its static position of a small distance. When an individual X-ray source tube has a speed that equals to group speed but an opposite moving direction, the individual X-ray source tube is triggered through an external exposure control unit. This arrangement allows the X-ray source tube to stay relatively standstill during the X-ray pulse trigger exposure duration. Multiple X-ray source tubes result in a much-reduced source tube travel distance for individual X-ray source tube. X-ray receptor is an X-ray flat panel detector. 3D radiography image projection data can be acquired with an overall much wider sweep in a much shorter time period, and image analysis can also be done in real-time while the scan goes.

In another aspect, an X-ray imaging system using multiple pulsed X-ray source tube in motion to perform highly efficient and ultrafast 3D radiography includes multiple pulsed X-ray source tube mounted on a structure in motion to form an array of sources. The multiple X-ray source tube moves simultaneously relative to an object on a predefined arc track at a constant speed as a group. Each individual X-ray source tube can also move rapidly around its static position at a small distance. When an individual X-ray source tube has a speed that is equal to group speed, but with the opposite moving direction, the individual X-ray source tube and X-ray detector are activated through an external exposure control unit. This arrangement allows the X-ray source tube to stay relatively standstill during the X-ray source tube activation and X-ray detector exposure. X-ray receptor is an X-ray flat panel detector. Multiple X-ray source tube in motion operation results in a much-reduced source travel distance for individual X-ray source tube. 3D radiography image data can be acquired with an overall wider sweep angle in a much shorter time, and image analysis can also be done in real-time while the scan goes.

In implementations, the X-ray source tube can also be randomly activated from one of any sources in the array using a random-firing scheme. Results of each and accumulated analysis determine the next X-ray source tube and exposure condition. 3D X-ray radiography images are reconstructed based on each image with an angled geometry of X-ray exposure source tube. Much broader applications include 3D mammography or Tomosynthesis, chest 3D radiography for COVID or fast 3D NDT, fast 3D X-ray security inspection.

Advantages of the above systems may include one or more of the following. The various embodiment of multiple X-ray source tube in motion is used in a novel ultrafast 3D radiography system. The first advantage is that system overall is several times faster. Each x-ray source tube would only need to mechanically travel a small fraction of the whole distance in an arc trajectory. It greatly reduces the amount of data acquisition time that is needed for a patient at the X-ray diagnosis machine. The second advantage is that image analysis can also be done in real-time as the scan goes. Judgment on the images taken will have an impact on the X-ray source tube position for the next shot. There is no need to wait until the finish of the whole image acquisition to do layered image reconstruction. The third advantage is that acquiring high resolution and high contrast images is possible due to the reduction of motion artifacts. Each X-ray source tube is also mounted on a substructure that vibrates the source around its origin. The composition of vibration speed and track speed leads to the relative standstill position of the X-ray source tube at the moment the individual X-ray source tube is activated. The fourth advantage is that the system can go with a much wider sweeping angle to acquire more data projections faster. More data projections mean better image construction that would lead to a reduced misdiagnosis rate. The fifth advantage is that because of a wider sweeping angle and faster imaging acquisition, it is possible to add time components to 3D spatial imaging to form a 4D imaging data set. The present invention has been described in terms of the preferred embodiment. It is recognized that equivalents, alternatives, and modifications, aside from those expressly stated, are possible and within the scope of the appending claims.

BRIEF DESCRIPTION

DETAILED DESCRIPTION

Figure 1:
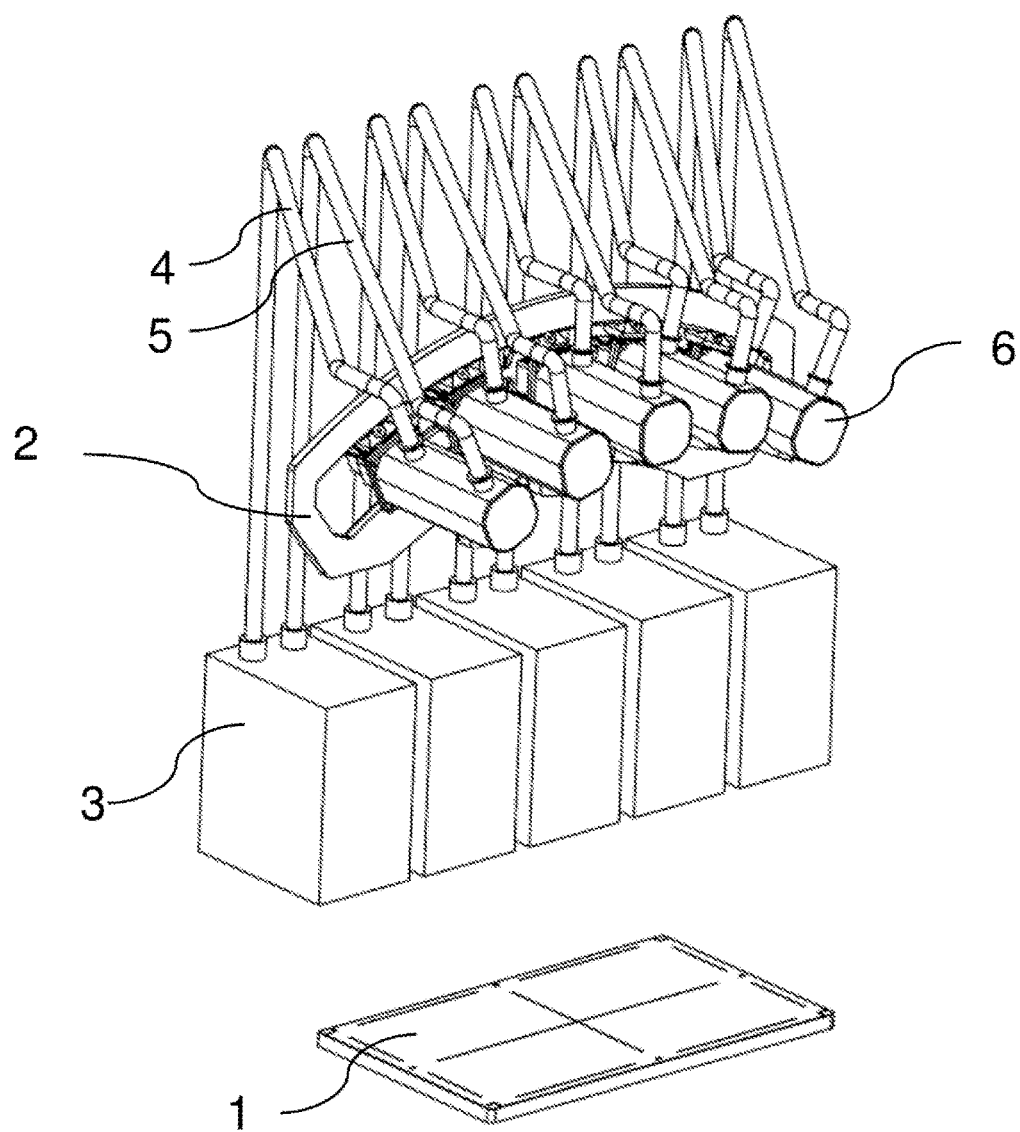
FIG. 1 illustrates an exemplary ultrafast 3D digital radiography system with multiple X-ray source tube in motion when an X-ray source has a separate high voltage unit and oil cooling unit.

In the following paragraphs, the present invention will be described in detail by way of example with reference to the attached drawings. Throughout this description, the preferred embodiment and examples shown should be considered exemplars rather than limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Fast 3D Radiography with multiple pulsed source X-ray source tube in motion is detailed below. In this system, multiple X-ray source tubes 9 from multiple pulsed X-ray sources are mounted on primary motion stage 8 to form an array of X-ray tubes 9. The multiple X-ray source tubes on the primary motion stage 8 move simultaneously relative to an object on a pre-defined arc track at a constant speed as a group. Each individual X-ray source tube in X-ray source can also move rapidly around its static position at a small distance. When an X-ray source tube 9 has a speed equal to group speed but with opposite moving direction, the X-ray source tube 9 and X-ray flat panel detector 1 are activated through an external exposure control unit so that tube stays momentarily standstill. It results in much-reduced travel distance for each X-ray source and a much lighter load for motion system. 3D scan can cover a much wider sweep angle in a much shorter time, and image analysis can also be done in real-time. An X-ray source usually comprises high voltage control electronics, high voltage cable 4, cooling system, oil cooling hoses 5, and X-ray source tube 9. A set of X-ray source is usually heavy weighted with heavy metal parts such as lead shielding. For a compact system, it is possible to put a set of X-ray source on motion control. However, to put one set of heavy X-ray source on motion stage is not practical. In this case, it is only necessary to vibrate X-ray source tube 9 part of an X-ray source, not vibrate the entire X-ray source. Motion control would then have much less load and with much better motion accuracy. With the conventional tube in a high voltage oil tank 3, it is possible to only vibrate X-ray source tube 9 in the tube housing 6. The present system separates the X-ray source tube 9 and electronics and vibrates only X-ray source tube 9 parts with high voltage cable 4 and oil cooling hose 5 connected, resulting in a more compact and reliable system.

FIG. 1 illustrates an ultrafast 3D digital radiography system with multiple X-ray source tubes 9 in motion when X-ray source has a separate high voltage unit and oil cooling unit. Generally, there are two kinds of X-ray sources. When X-ray source power is larger, X-ray source has a separate high voltage unit and oil cooling unit. When X-ray source power is relatively small, the X-ray source tube, high voltage, and oil cooling are usually in the same housing, sometimes called a mono-block.

In FIG. 1 configuration, X-ray source has a separate high voltage oil tank 3 and oil cooling unit. The ultrafast 3D digital imaging system comprises X-ray detector 1, multiple pulsed sources, frame structure 2, high voltage oil tank 3, high voltage cable 4, oil cooling hose 5, X-ray source tube housing 6, etc. An X-ray source tube 9 is in X-ray stand-alone tube housing 6. An X-ray source tube housing 6 is mounted on secondary motion stage 7. All secondary motor stages 7 are mounted at the primary motor stage 8.

Each secondary motor stage 7 is engaged to a secondary motor. All secondary motion stages 7 are mounted on a primary motion stage 8. Every X-ray stand-alone tube housing 6 is mounted on a secondary motor stage 7. Every motor is controlled by programmable motion control hardware and can move the motor stage back and forth at a predetermined speed. The secondary motor stages 7 are positioned in such a way that spacing to adjacent stages is equal. As a result, all X-ray source tube cases move together with the primary motor stage 8, but each individual X-ray source tube 9 can also move individually with individual secondary motor stage 7.

The X-ray flat panel detector 1 can also be mounted on an additional linear stage. The X-ray flat panel detector 1 can also move back and forth, based on the location of the X-ray source tube 9 in order to have a broader coverage of images.

During operation, the X-ray flat panel detector 1 receives X-ray and send imaging data to computer. The array of multiple X-ray sources is mounted on a primary motion stage 8 through secondary motor stage 7. The primary motion stage 8 moves simultaneously relative to an object on a predefined arc track at a constant speed. As a group each individual X-ray source is also mounted on a substructure that vibrates the source around its origin. The composition of vibration speed and track speed leads to the relative standstill position of the X-ray source at the moment the individual X-ray source is activated. A primary motor engages with the primary motor stage 8 and controls the speed of the primary motor stage 8. The array of multiple X-ray sources is each moved by a secondary motor stage 7 coupled to the primary motor stage 8. A plurality of secondary motors each engages a secondary motor stage 7 and controls the speed of secondary motor stage 7. In the secondary motor stages 7, each secondary motor stage 7 has a motor driver to control the driving frequency of the secondary motor stage 7. Each X-ray source includes an X-ray source tube 9 with an electrical switch connected to a power supply.

Multiple pulsed source frame structure 2 includes multiple source frame segments. Each has multiple pulsed X-ray source tube sources. A plurality of source segment holders is used to hold the individual source segments at a predetermined location in a certain shape of arc. An overall group of sources is held by an overall structure designed to move along the direction of an arc. An arc rail with a predefined curvature is provided as a guide and track to support the motion of the overall structure. A primary motor stage 8 is moved along the direction of the arc rail with a high precision stage system. A corresponding motor controller controls the speed of the primary motor stage 8. Individual secondary motor stages 7 are mounted on top of the individual source segments. Each of the secondary motor stages 7 engages with a corresponding secondary motor to control its speed. A source activating controller is connected to each X-ray source tube 9 and the X-ray flat panel detector 1 in order to trigger X-ray detector 1 and each X-ray source tube 9 individually.

Next, the operation of 3D radiography based on one array of pulsed X-ray source tubes is detailed. The moving X-ray source tube 9 provides an ultrafast 3D radiography imaging technique with a significant reduction in travel distance of each X-ray source tube relative to its original location. A single stationary X-ray flat panel detector 1 receives X-ray flux from the array of X-ray source tubes 9 and generates radiography data, and projection image data are reconstructed with each X-ray source tube 9 as an individual source that travels along an arc segment trajectory relative to the object. An X-ray source tube 6, a flat panel detector 1, and the three-dimensional positioning accuracy of the entire structure can be determined by using the round rail length curvature radius center to center distance between primary motor stage 8 and secondary motor stage 7 and angular deviation from a straight line.

Oil cooling tank has cooling channels with small heat exchangers in the middle. The rotor blades inside each channel will spin to produce forced convection to transport the oil heat away from the pre-cooler surface. This prevents thermal shock and surface defects on the cooled materials due to non-uniform temperatures. Heating each rotor blade channel can have an independent pumping system to allow one to operate while another is down for repair or maintenance.

The X-ray stand-alone tube housing 6 includes an X-ray generating source assembly and a tube wall. The X-ray generating source assembly is an internal unit within the X-ray stand-alone tube housing 6. The X-ray generating source assembly includes an X-ray beam that can pass through the tube wall to provide X-ray radiography for various applications. The X-ray stand-alone tube housing 6 may be made of a metal material such as aluminum alloy alternatively.

Figure 2:
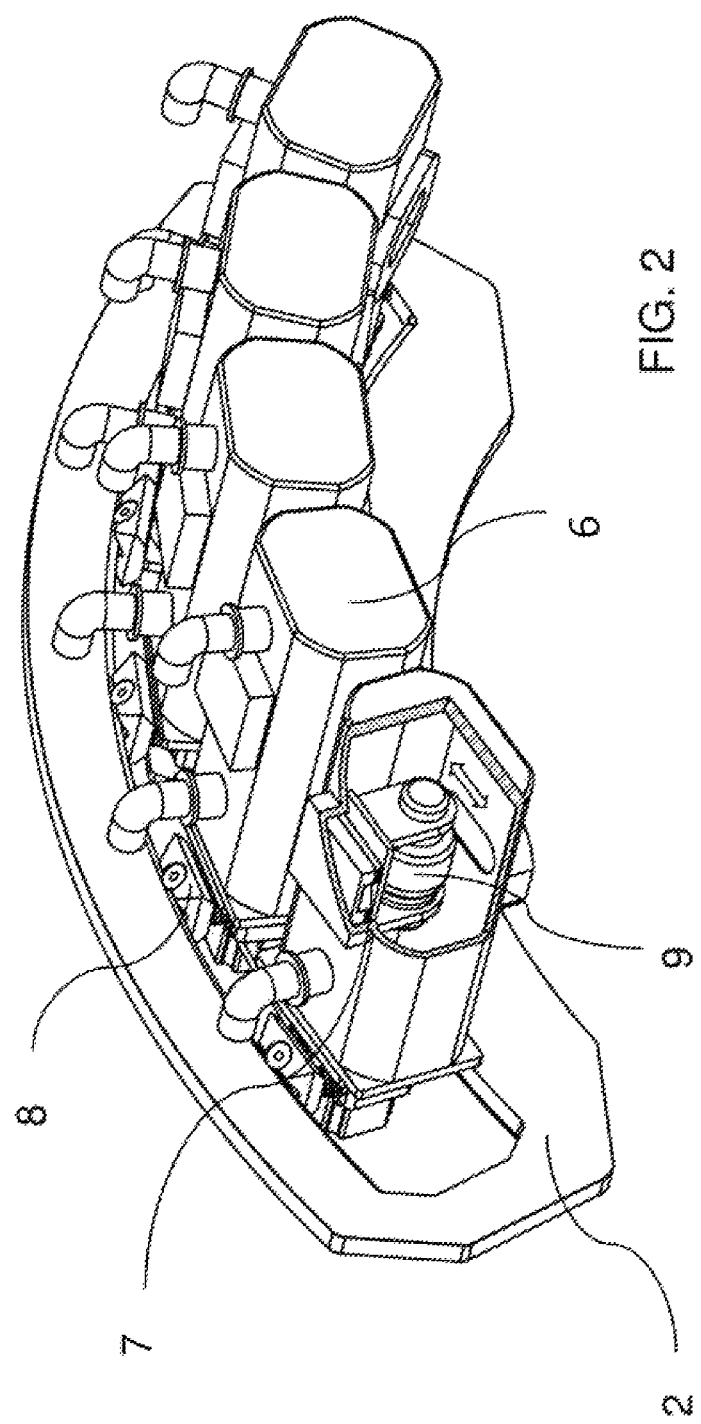
FIG. 2 illustrates an exemplary ultrafast 3D digital radiography system with multiple X-ray source tube in motion when an X-ray source tube is in a housing unit.

FIG. 2 illustrates an ultrafast 3D digital radiography system with multiple X-ray source tubes 9 in motion when X-ray source tube high voltage and oil cooling are in the same housing. In this case, X-ray source tube housing 6 is mounted at primary motion stage 8 while X-ray source tube 9 is mounted at secondary motor stage 7. Primary motion stage 8 is mounted at multiple pulsed source frame structure 2.

X-ray source tube housing 6 with a plurality of multiple pulsed X-ray source tube 9 is mounted on a structure in motion to form an array of sources. The housing moves with the structure at a constant speed around an object in 3D space. Each individual X-ray source tube 9 can also move rapidly around its static position of a small distance. When an individual X-ray source tube 9 has a speed that equals to group speed but an opposite moving direction the individual X-ray source tube 9 is triggered through an external exposure control unit. This arrangement allows the X-ray source tube 9 to stay relatively standstill during the X-ray pulse trigger exposure duration. Multiple X-ray source tubes 9 result in a much-reduced source travel distance for individual X-ray source tube 9. X-ray receptor is an X-ray flat panel detector 1, 3D radiography image projection data can be acquired with an overall much wider sweep in a much shorter period, and image analysis can also be done in real-time while the scan goes. The present invention includes a method system and or computer program product. In one embodiment, the method system and or computer program product may be implemented in the context of mammography breast imaging.

Primary motion stage 8 holds X-ray source tube 9 in motion secondary motor stages and flat-panel detector. Each X-ray source tube in motion is mounted on the primary motion stage with motorized motion. While each of the secondary motor stages also carries its secondary motor to oscillate it around an arc path according to a predefined arc track with constant speed as a group. There are multiple X-ray source tubes 9 in motion simultaneously, which means all X-ray source tubes 9 moves at the same speed but each X-ray source tube 9 vibrates independently. The group of X-ray source tubes will scan across the human body together as a single unit.

X-ray tube 9 generates imaging data using multiple pulsed X-ray source tube 9 in motion to perform ultrafast, high-efficient 3D radiography. Multiple pulsed X-ray source tubes 9 are mounted on a structure in motion to form an array of the source. The multiple X-ray source tubes 9 move simultaneously around an object on a pre-defined track at a constant speed of a group. Each individual X-ray source tube can also move rapidly around its static position of a small distance when an individual X-ray source tube has a speed that equals group speed. But an opposite moving direction, the individual X-ray source tube is triggered through an external exposure control unit. This arrangement allows the X-ray source tube 9 to stay relatively standstill during the X-ray pulse trigger exposure duration. Multiple X-ray sources result in a much-reduced source travel distance for individual X-ray source tube 9. X-ray receptor is an X-ray flat panel detector 1. X-ray 3D radiography image projection data can be acquired with an overall much wider sweep in a much shorter time, and image analysis can also be done in real-time. While the scan goes in another aspect, an X-ray imaging system applies the multiple pulsed X-ray source tube in motion to perform highly efficient and ultrafast 3D radiography.

Secondary motor stage 7 move simultaneously with primary motor stage 8 of a constant speed. The number of secondary motor stages 7 is the same as that of X-ray sources. X-ray flat panel detector 1 receives X-ray flux generated from X-ray sources and gets starting signals for image acquisition and then sends data to computer to perform analysis of image data.

Multiple pulsed source frame structure 2 is the main part of a supporting frame structure as shown in F. 2. Multiple pulsed X-ray source tubes 9 from X-ray sources are moved by a secondary motor stage 7 controlled by a secondary motor. A primary motor stage 8 with a primary motor engages with the main motor and controls. An X-ray flat panel detector 1 to receive X-ray flux and send imaging data is installed at the end of the system. In front of the system, primary motor stage 8 and secondary motor stages 7 are all mounted on the supporting frame structure 2.

Figure 3:
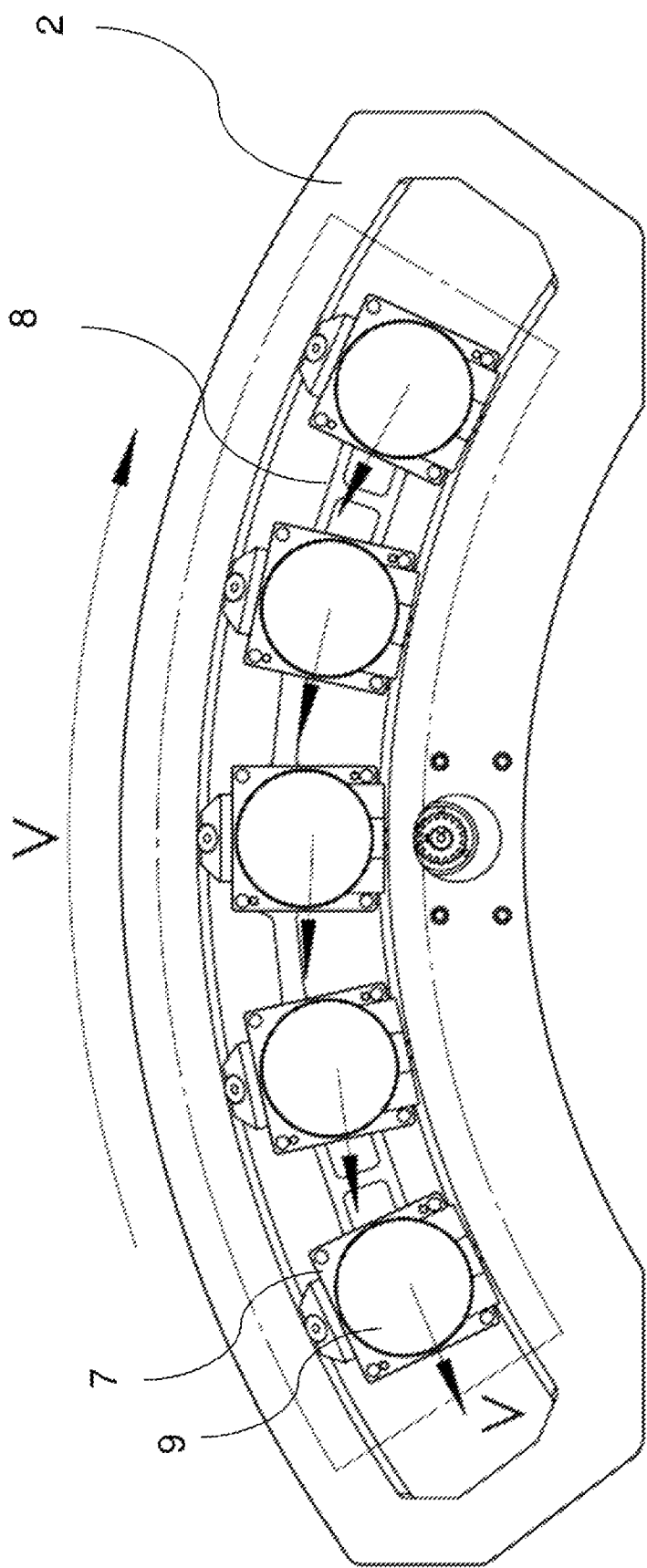
FIG. 3 illustrates an exemplary configuration where an individual X-ray source tube emits an X-ray beam in a temporary standstill position at the moment when the primary and secondary motor stages are moving in the opposite direction but with the same speed.

FIG. 3 illustrates that an individual X-ray source tube 9 emits an X-ray beam in a temporary standstill position at the moment when the primary motor stage 8 and secondary motor stages 7 are moving in the opposite direction but with the same speed. For one data acquisition cycle, primary motor stage 8 moves in one direction at a constant speed, then go back to the initial position. While primary motor stage 8 is moving at a constant speed, secondary motor stage 7 vibrates at the predetermined speed. When secondary motor stage 7 travels in the opposite direction to the primary motion stage 8 and has the same constant speed, X-ray source tube 9 and X-ray flat panel detector 1 are triggered. At this moment of a trigger, an X-ray source tube 9 behaves just like the X-ray source tube 9 is standstill while emitting an X-ray beam to keep focal spot size minimal so that X-ray image can be sharp. Therefore, the dynamic arrangement of stationary state an X-ray source tube 9 allows an X-ray imaging system to acquire a large number of images from different spatial angle locations in a very short amount of time. Duration of constant speed motion of a secondary motor stage 7 can be programmed by software to match X-ray exposure time. When one secondary motor stage 7 is at the constant speed, the other secondary motor stage 7 could be in acceleration, deceleration, or move back to the initial position to get ready for their next constant speed. X-ray source tubes 9 can also be programmed to perform exposure on-demand based on each independent external trigger pulse in a random sequence. In view of the widely available superfast computer available, image analysis can be done in real-time with the image acquisition. Judgment on the images taken will impact the X-ray source tube 9 position for the next shot. There is no need to wait until finish of the whole image acquisition to do image reconstruction.

Primary motor stage 8 is mounted on a platform that can move freely along the arc rail with a predetermined shape. A motor engaged with the primary motor stage 8 is used to control the primary motor stage travel speed. The control unit sends command signals to a plurality of secondary motor stages 7 through a control line. Control signals are managed by an external operator and command the secondary motor stages 7 to oscillate on the same arc track with a selected speed.

Secondary motor stage 7 also serves as a carrier for a series of X-ray source tubes 9. Each of the X-ray source tubes 9 can be actuated to emit X-rays via a high voltage electrical power source and are coupled to a source of electrical power through which X-rays pass and impinge on an object. In the form of pulse beams and then X-ray imaging data generated from the interaction between the X-rays and the object are captured by detector image reconstruction software processes. The X-ray imaging data into a reconstructed 3D image of the object with various 3D radiographic images projected onto an external monitor.

Figure 4:
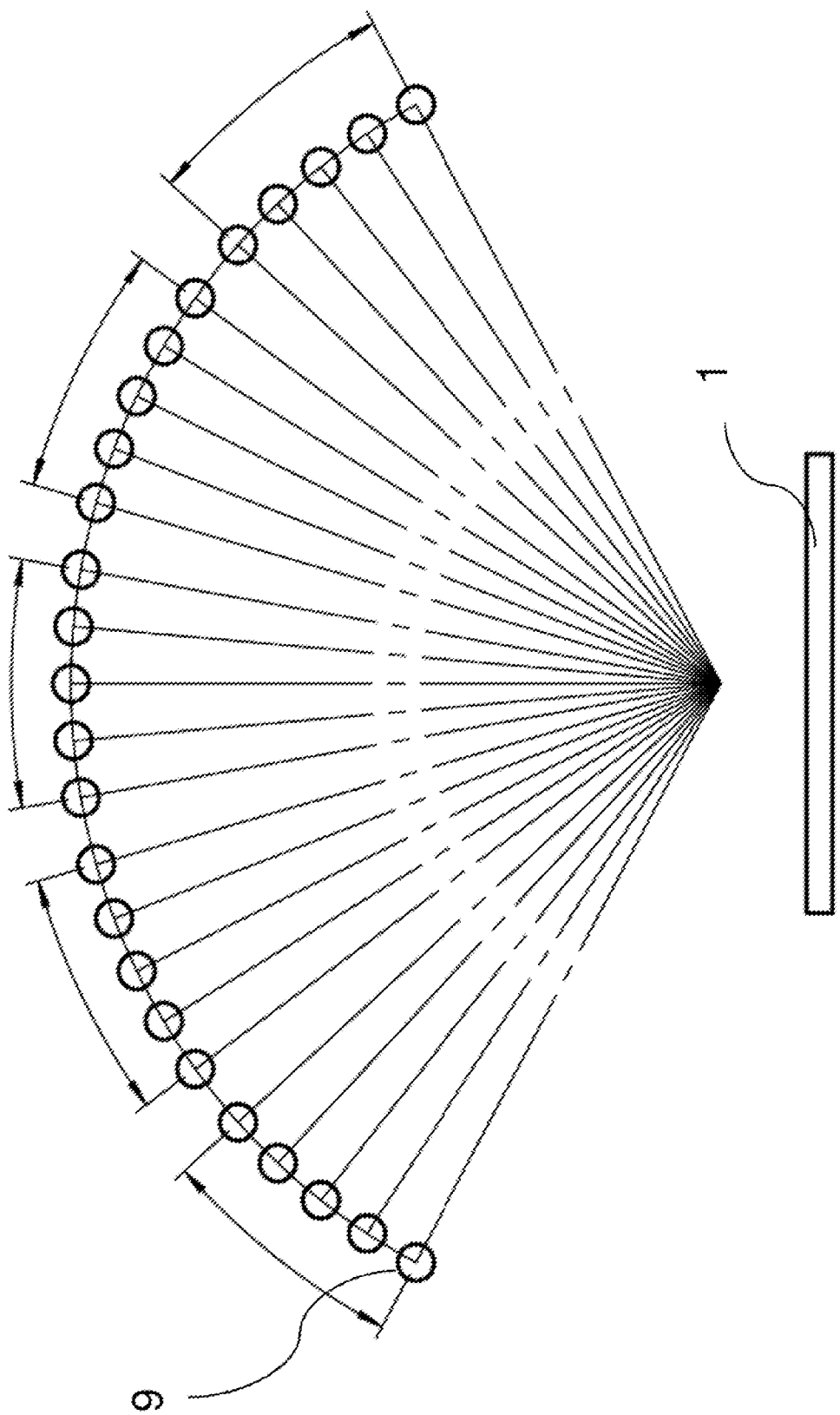
FIG. 4 illustrates an exemplary five-X-ray-source-tube configuration that takes 25 sets of projection data by each X-ray source tube traveling only one-fifth of the total distance.

FIG. 4 illustrates an exemplary five-X-ray-source-tube configuration that takes 25 sets of projection data by each traveling only one-fifth of the total distance. In this implementation, there are five X-ray source tubes 5 working in parallel and the five X-ray source tubes 5 perform 25 total X-ray exposures at different angle positions. But each secondary motor stage 7 only needs to travel one-fifth of the total covered angle. Therefore, with multiple X-ray source tubes 9 working in parallel, a large amount of projection data can be acquired at a fraction of amount of time. X-ray flat panel detector 1 is served as an X-ray receiver. Electronic signals always go faster than mechanical motion so that bottleneck is always from mechanical side.

X-ray flat panel detector 1 is positioned on X-ray stage. The X-ray stage can also move freely around an arc-shaped rail of the X-ray source tube 9 to have better exposure angle. That is controlled by a controller unit that allows the X-ray source tube 9 to move relative to X-ray flat panel detector 1 and X-ray stage or fixed position.

Multiple X-ray source tubes 9 and corresponding X-ray detector allow the X-ray source tube to stay relatively standstill during the X-ray pulse trigger exposure duration. Multiple X-ray source tubes 9 result in a much-reduced source travel distance for individual X-ray source tube 9. As a result, the 3D projection image data can be acquired with an overall much wider sweep angle in a much shorter time, and image analysis can also be done in real-time.

The system to provide fast 3D radiography using multiple pulsed X-ray source tube in motion includes a primary motor stage 8 moving freely on an arc rail with a predetermined shape. The primary motor engages with said primary motor stage 8 and controls the speed of the primary motor stage 8. A plurality of secondary motor stages 7 coupled to said primary motor stage 8 moves along the arc rail direction. A plurality of secondary motors each engages a secondary motor stage 7 and controls the secondary motor stage's speed. A plurality of X-ray source tubes 9 from X-ray sources are each moved by a secondary motor stage 7. A supporting frame structure provides housing for the primary motor and secondary motor stages 7 and a flat panel detector 1. A method of fast 3D radiography using multiple pulsed X-ray source tube in motion comprising positioning a primary motor stage 8 and one or more secondary motor stages 7 to a predetermined initial location, sweeping the primary motor stage 8 at a predetermined constant speed by said primary motor oscillating each of the secondary motor stages 7 by a corresponding secondary motor with a predetermined sequence, then electrically activating an X-ray source tube 9 and a flat panel detector 1 when a secondary motor stage 7 moves in an opposite direction to that of the primary motor stage 8 and at a selected speed of the primary motor stage 8, and then acquiring image data from the X-ray flat panel detector 1.

Primary motor controls the position and speed of the primary motor stage 8 along an arc track. It is also responsible for rotating or translating the entire multiple pulsed X-ray source tube 9 in motion. A pre-defined arc track in alternative implementations can also provide rotation to an array of multiple pulsed X-ray source tubes 9.

While various embodiments of the present invention have been described above, it should be understood that they have been presented by way of example only and not of limitation. The various diagrams may depict an example architectural or other configuration for the invention, which is done to understand the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical, or physical partitioning and configurations may be implemented to implement the desired features of the present invention. Also, a multitude of different constituent module names other than those depicted herein may be applied to the various partitions. Additionally, with regard to flow diagrams, operational descriptions, and method claims, the order in which the steps are presented herein shall not mandate that various embodiments be implemented to perform the recited functionality in the same order unless the context dictates otherwise.

The presence of broadening words and phrases such as "one or more," "at least," "but not limited to" or other such as phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

What is claimed is:

1. A system to provide fast 3D radiography using multiple pulsed X-ray source tubes in motion, comprising:
   a primary motor stage moving freely on an arc rail with a predetermined shape;
   a primary motor that engages with said primary motor stage and controls a speed of the primary motor stage;
   a plurality of secondary motor stages coupled to said primary motor stage and move along a direction of the arc rail;
   a plurality of secondary motors, each engaging a secondary motor stage and controlling speed of secondary motor stage;
   a plurality of X-ray source tubes each moved by a secondary motor stage;
   a supporting frame structure that provides housing for the primary motor stage and secondary motor stages; and
   an X-ray flat panel detector to receive X-ray flux and send imaging data.

2. The system of claim 1, comprising:
   a predefined track; and
   a source array including multiple pulsed X-ray source tubes mounted on a structure in motion, wherein each of the multiple pulsed X-ray source tubes moves simultaneously around an object on the pre-defined track at a constant speed of a group, and when an individual X-ray source tube has a speed that equals to group tube speed but in an opposite moving direction, the individual X-ray source tube is triggered through an exposure control unit.

3. The system of claim 1, wherein a speed or a position of the primary motor stage and secondary motor stages are adjustable by software.

4. The system of claim 1, wherein the current and voltage of an X-ray source tube are adjustable by software.

5. The system of claim 1, wherein exposure time of X-ray source tube is adjustable by software.

6. The system of claim 1, wherein the X-ray source tube stands still relative to the X-ray flat panel detector during an X-ray pulse trigger exposure duration.

7. The system of claim 1, wherein the X-ray flat panel detector acquires 3D radiography image projection data with a predetermined sweep over a predetermined time period, and wherein image reconstruction is done in real-time during scanning.

8. The system of claim 1, wherein the object is at a standstill.

9. The system of claim 1, wherein the result of each and accumulated analysis determines the next X-ray source tube and exposure condition.

10. A system, comprising:
    an X-ray exposure control unit;
    a predefined track; and
    a source array including multiple pulsed X-ray source tubes mounted on a structure in motion, wherein each of the multiple pulsed X-ray source tubes moves simultaneously around an object on the pre-defined track at a constant speed of a group, and when an individual X-ray source tube has a speed that equals to group tube speed but in an opposite moving direction, the individual X-ray source tube is triggered through the exposure control unit; and
    an X-ray flat panel detector to receive X-ray flux and send X-ray imaging data.

11. The system of claim 10, wherein the current and voltage of an X-ray source tube are adjustable by software.

12. The system of claim 10, wherein exposure time of X-ray source tube is adjustable by software.

13. The system of claim 10, wherein the flat panel detector acquires 3D radiography image projection data with a predetermined sweep over a predetermined time, and wherein image reconstruction is done in real-time during scanning.

14. The system of claim 10, the X-ray source tube can be activated using a predetermined scheme.

15. The system of claim 10, wherein the object is at a standstill.

16. A method of fast 3D radiography using multiple pulsed X-ray source tubes in motion, comprising:
- using multiple pulsed X-ray source tubes in motion by positioning a primary motor stage and multiple secondary motor stages to a predetermined initial location;
- sweeping the primary motor stage at a predetermined constant speed by said primary motor;
- oscillating each of the secondary motor stages by a corresponding secondary motor with a predetermined sequence;
- electrically activating both an X-ray source tube and an X-ray flat panel detector when a secondary motor stage moves in an opposite direction to that of the primary motor stage and at a selected speed of the primary motor stage; and
- acquiring image data from the X-ray source tube with an X-ray flat panel detector.

17. The method of claim 16, wherein the X-ray flat panel detector acquires 3D radiography image projection data with a predetermined sweep over a predetermined time, and wherein image reconstruction is done in real-time during scanning.

18. The method of claim 16, comprising changing an X-ray source voltage output based on object density during a sweep.

19. The method of claim 16, wherein 4D imaging is performed by adding a time component to 3D spatial imaging data.

20. The method of claim 16, comprising changing a sweep angle based on a region of interest.

* * * * *